United States Patent [19]
Bastian et al.

[11] Patent Number: 5,769,854
[45] Date of Patent: Jun. 23, 1998

[54] INSTRUMENT SYSTEM FOR PREPARING A DISTAL FEMUR FOR A POSTERIORLY STABILIZED FEMORAL COMPONENT OF A KNEE PROSTHESIS

[75] Inventors: Adam C. Bastian, Westwood, N.J.; Marc G. Weissman, Derby, Conn.; Michael E. Wolak, Leonia, N.J.

[73] Assignee: Osteonics Corp., Allendale, N.J.

[21] Appl. No.: 703,597

[22] Filed: Aug. 23, 1996

[51] Int. Cl.⁶ .......................... A61B 17/58; A61B 17/60
[52] U.S. Cl. .............................. 606/88; 606/82; 606/83; 606/89
[58] Field of Search ................. 606/82, 83, 88, 606/89, 87, 96, 102

[56] References Cited

U.S. PATENT DOCUMENTS

| | | |
|---|---|---|
| 4,719,908 | 1/1988 | Averill et al. . |
| 4,721,104 | 1/1988 | Kaufman et al. . |
| 4,892,093 | 1/1990 | Zarnowski et al. ........................ 606/88 |
| 5,007,933 | 4/1991 | Sidebotham et al. ...................... 623/18 |
| 5,098,436 | 3/1992 | Ferrante et al. . |
| 5,100,409 | 3/1992 | Coates et al. . |
| 5,176,684 | 1/1993 | Ferrante et al. . |
| 5,405,349 | 4/1995 | Burkinshaw et al. . |
| 5,415,662 | 5/1995 | Ferrante et al. . |
| 5,569,260 | 10/1996 | Petersen ..................................... 606/88 |
| 5,593,411 | 1/1997 | Stalcup et al. ............................ 606/88 |

Primary Examiner—Paul B. Prebilic
Attorney, Agent, or Firm—Arthur Jacob

[57] ABSTRACT

An instrument system and method are disclosed for preparing a distal femur for the implant of a femoral component of a knee prosthesis by the removal of natural bone in the intercondylar area of the distal femur to prepare a femoral notch, including a patella recess, subsequent to establishing distal, anterior and chamfer surfaces at the distal femur. The instrument system includes a femoral notch cutting guide for placement over the distal, anterior and chamfer surfaces of the prepared distal femur, and a femoral notch cutting punch. The femoral notch cutting punch is engaged with a first guideway in the femoral notch cutting guide to remove natural bone from the intercondylar area and establish the patella recess, and subsequently is engaged with a second guideway in the femoral notch cutting guide, transverse to the first guideway, to remove natural bone from the intercondylar area and complete the femoral notch.

17 Claims, 6 Drawing Sheets

INSTRUMENT SYSTEM FOR PREPARING A DISTAL FEMUR FOR A POSTERIORLY STABILIZED FEMORAL COMPONENT OF A KNEE PROSTHESIS

The present invention relates generally to the implant of prosthetic joints and pertains, more specifically, to an instrument system and method for preparing a distal femur for the reception of a posteriorly stabilized femoral component of a knee prosthesis.

Posteriorly stabilized prosthetic knee implants are employed where ligaments which normally stabilize the natural knee no longer are available to stabilize the prosthetic knee implant, either through weakening of the ligaments as a result of disease or injury, or through sacrifice of certain ligaments during the implant procedure itself. One such posterior stabilized knee implant is disclosed in U.S. Pat. No. 5,007,933, to Sidebotham et al, the disclosure of which patent is incorporated herein by reference thereto.

In order to prepare the distal femur appropriately for the reception of a posteriorly stabilized femoral component, it is necessary to remove natural bone from the intercondylar area of the distal femur so as to prepare a femoral notch within which the posteriorly stabilizing structure of the femoral component is located. Additionally, the femoral notch includes a patella recess for assuring proper functioning of the patella upon completion of the implant procedure.

The present invention provides an instrument system and method for preparing the required femoral notch, with the appropriate patella recess, in an effective manner and, as such, attains several objects and advantages, some of which are summarized as follows: Effects the removal of intercondylar bone with greater ease and increased accuracy for facilitating preparation of the femoral notch; enables the creation of a complete femoral notch, including an appropriate patella recess, more quickly, to the benefit of both the surgeon and the recipient of the prosthetic knee implant; provides an instrument system and method having less complexity for increased ease of use; simplifies the procedure for preparing a distal femur for the reception of a posteriorly stabilized femoral component; enables accuracy in the removal of only that amount of natural bone necessary for proper accommodation of the femoral component, thereby minimizing trauma to the bone while maximizing performance of the femoral component; assures proper fitting of the femoral component for exemplary performance over a long service life.

The above objects and advantages, as well as further objects and advantages, are attained by the present invention which may be described briefly as an instrument system for preparation of a longitudinally extending natural bone for the implant of a component of a prosthesis, the preparation including removal of natural bone to prepare a notch in the natural bone subsequent to the execution of cuts establishing corresponding surfaces on the natural bone, the instrument system comprising: a notch cutting guide for placement over the surfaces of the prepared natural bone, the notch cutting guide having surfaces for overlying corresponding surfaces of the natural bone, the notch cutting guide including a first guideway extending along the notch cutting guide in a direction transverse to the longitudinal extent of the natural bone, and a second guideway extending along the notch cutting guide in a generally longitudinal direction; and a notch cutting punch having a length extending between opposite ends, a cutting edge at one of the opposite ends, and coupling means at the other of the opposite ends, the notch cutting punch including follower means extending along the length of the notch cutting punch, the follower means being complementary to each of the first and second guideways such that upon engagement of the follower means with the first guideway and the application of a cutting force at the coupling means the notch cutting punch is advanced transversely, to remove natural bone and establish a portion of the notch, and upon engagement of the follower means with the second guideway and the application of a further cutting force at the coupling means, the notch cutting punch is advanced longitudinally, to remove natural bone to complete the notch.

In addition, the present invention includes a method for preparation of a longitudinally extending natural bone for the implant of a component of a prosthesis, the preparation including removal of natural bone to prepare a notch in the natural bone, the method comprising the steps of: executing cuts to establish corresponding surfaces on the natural bone; placing a notch cutting guide over the surfaces of the prepared natural bone, the notch cutting guide including a first guideway extending along the notch cutting guide in a direction transverse to the longitudinal extent of the natural bone, and a second guideway extending along the notch cutting guide in a generally longitudinal direction; providing a notch cutting punch having follower means extending along the length of the notch cutting punch, the follower means being complementary to each of the first and second guideways; engaging the follower means with the first guideway and applying a cutting force to the notch cutting punch to advance the notch cutting punch transversely, and remove natural bone to establish a portion of the notch; retracting the notch cutting punch to disengage the follower means from the first guideway; and engaging the follower means with the second guideway and applying a further cutting force to the notch cutting punch to advance the notch cutting punch longitudinally, and remove natural bone to complete the notch.

The invention will be understood more fully, while still further objects and advantages will become apparent, in the following detailed description of preferred embodiments of the invention illustrated in the accompanying drawing, in which:

Figure 1:
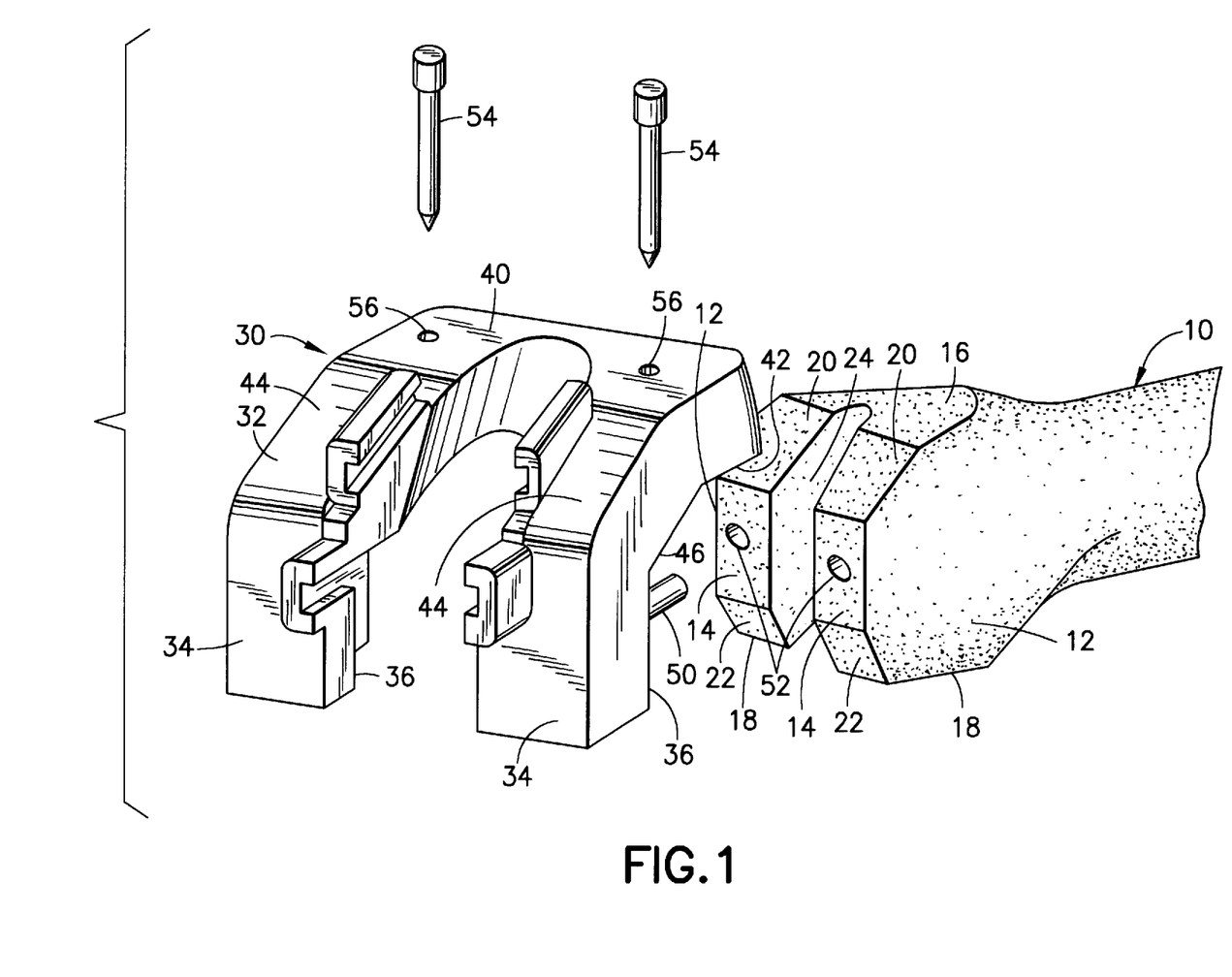
FIG. 1 is a perspective view of a component part of an instrument system constructed in accordance with the invention about to be placed upon a distal femur in accordance with the method of the present invention.

Referring now to the drawing, and especially to FIG. 1 thereof, a site for the implant of a prosthesis is illustrated in the form of a distal femur 10 which extends in a longitudinal direction, includes condyles 12, and has been prepared partially for the reception of a femoral component of a posteriorly stabilized prosthetic knee implant (not shown herein, however a typical posteriorly stabilized prosthetic knee implant is illustrated fully in the aforesaid U.S. Pat. No.

5,007,933) by the execution of five femoral cuts to establish corresponding cut surfaces on the distal femur 10, namely, distal surfaces 14 extending in lateral directions, an anterior surface 16 extending longitudinally along the distal femur 10, longitudinally extending posterior surfaces 18, and chamfer surfaces 20 and 22 extending at angles transverse to the distal, anterior and posterior surfaces 14, 16 and 18, all in a manner now well known and as disclosed, for example, in U.S. Pat. No. 4,892,093, incorporated herein by reference thereto. In order to accommodate the femoral component of the knee prosthesis to be implanted at the distal femur 10, natural bone is to be removed from intercondylar area 24 of the distal femur 10, utilizing an instrument system and method of the present invention.

Instrument system 30, constructed in accordance with the present invention, includes a femoral notch cutting guide 32 for placement over the prepared distal femur 10. Cutting guide 32 has a first portion 34 which includes a first surface 36 for overlying the distal surfaces 14, a second portion 40 which includes a second surface 42 for overlying the anterior surface 16, and a third portion 44 which includes a third surface 46 for overlying the chamfer surfaces 20, the first, second and third surfaces 36, 42 and 46 being complementary to the respective distal, anterior and chamfer surfaces 14, 16 and 20 as is common in such cutting guides. A pair of locator lugs 50 are integral with the first portion 34 of the cutting guide 32 and project in a longitudinal direction from the first surface 36 to engage complementary locator holes 52 in the distal femur 10 and thereby locate the cutting guide 32 on the distal femur 10, in a now well-known manner. Once the cutting guide 32 is located on the distal femur 10, as illustrated in FIG. 2, a pair of affixation pins 54 are inserted through complementary apertures 56 in the second portion 40 of the cutting guide 32 and into the distal femur 10 to secure the cutting guide 32 in place.

Figure 2:
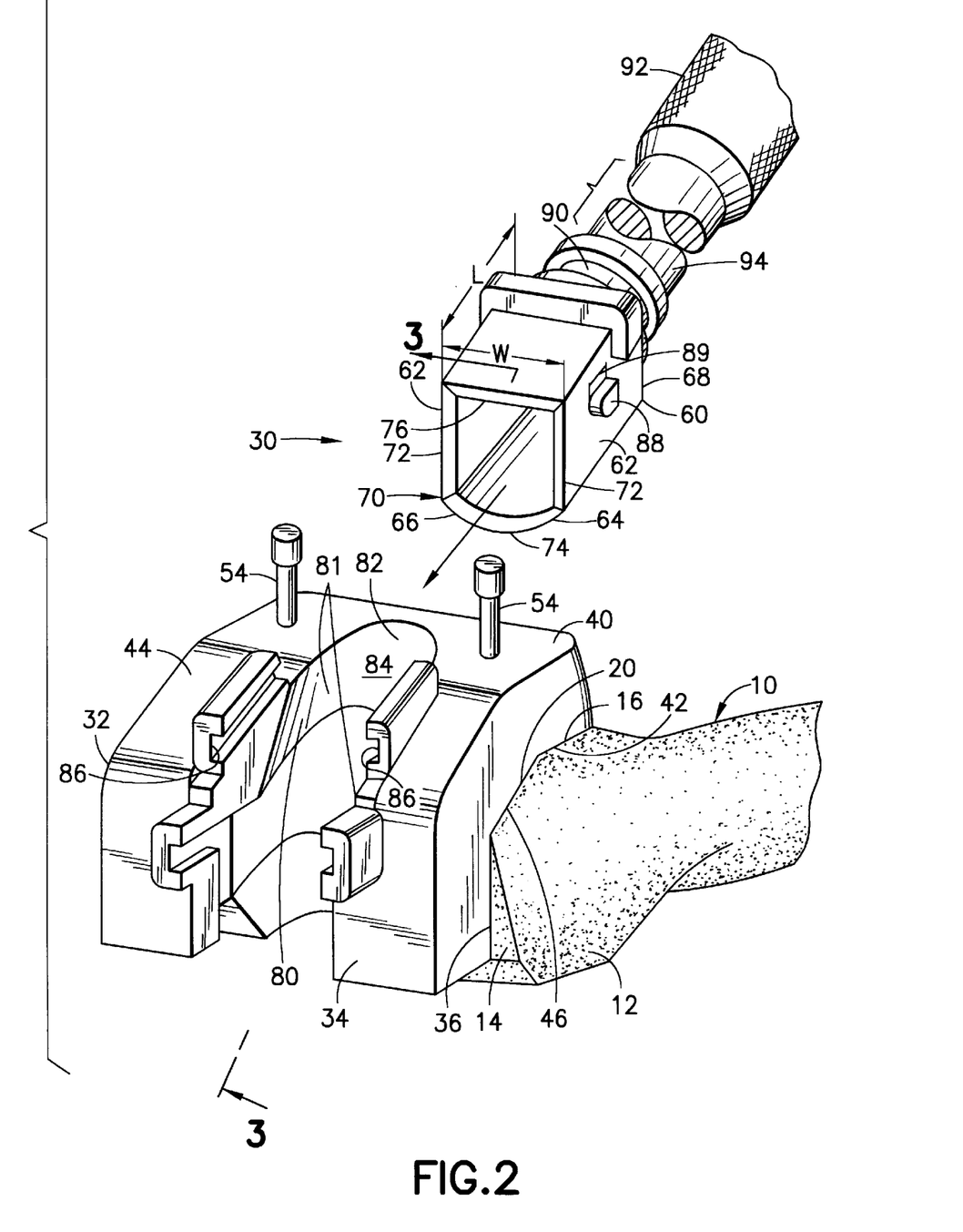
FIG. 2 is a perspective view similar to FIG. 1, showing another component part about to be inserted for establishing a patella recess.
Figure 3:
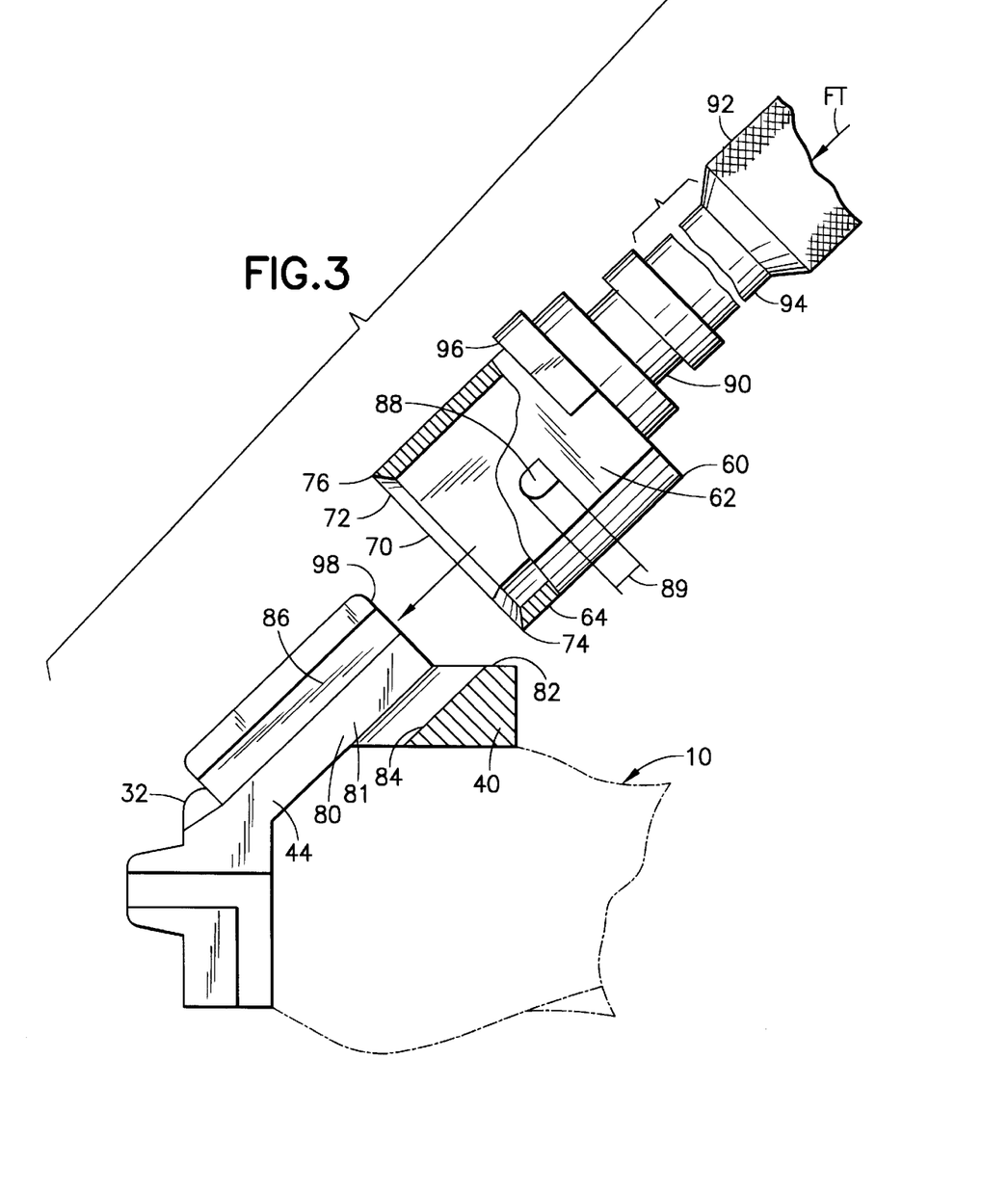
FIG. 3 is a cross-sectional view taken along line 3—3 of FIG. 2 with the distal femur illustrated in phantom, for clarity.

As best seen in FIG. 3, as well as in FIG. 2, instrument system 30 includes a femoral notch cutting punch 60 having opposite sides 62 spaced apart laterally to establish a width W, a curved face 64 between the opposite sides 62, and a length L extending longitudinally between opposite ends 66 and 68. A cutting edge 70 at end 66 includes opposite parallel straight cutting portions 72, a curved cutting portion 74 extending between the straight cutting portions 72, and a shorter straight cutting portion 76 extending between the straight cutting portions 72, opposite the curved cutting portion 74. A first channel 80 in the cutting guide 32 extends in a transverse direction along the third portion 44 of the cutting guide 32 and includes a width between opposite laterally spaced apart side walls 81, the width of channel 80 being generally complementary to the width W of the cutting punch 60, an entrance 82, a curved bottom 84, complementary to the curved face 64 of the cutting punch 60, and a first guideway in the form of first grooves 86 in the third portion 44, the first grooves 86 extending along the channel 80 in the transverse direction between the first portion 34 and the second portion 40 of the cutting guide 32. Follower means in the form of a spline 88 having a length 89 and extending longitudinally along each side 62 of the cutting punch 60 are complementary with first grooves 86 in the cutting guide 32, the first grooves 86 extending along the third portion 44 of the cutting guide 32, in the transverse direction between the first and second portions 34 and 40. Coupling means in the form of a threaded collar 90 at the other end 68 of the cutting punch 60 couple a handle 92 with the cutting punch 60, by means of a complementary threaded stud 94 on the handle 92, for purposes described below.

Figure 4:
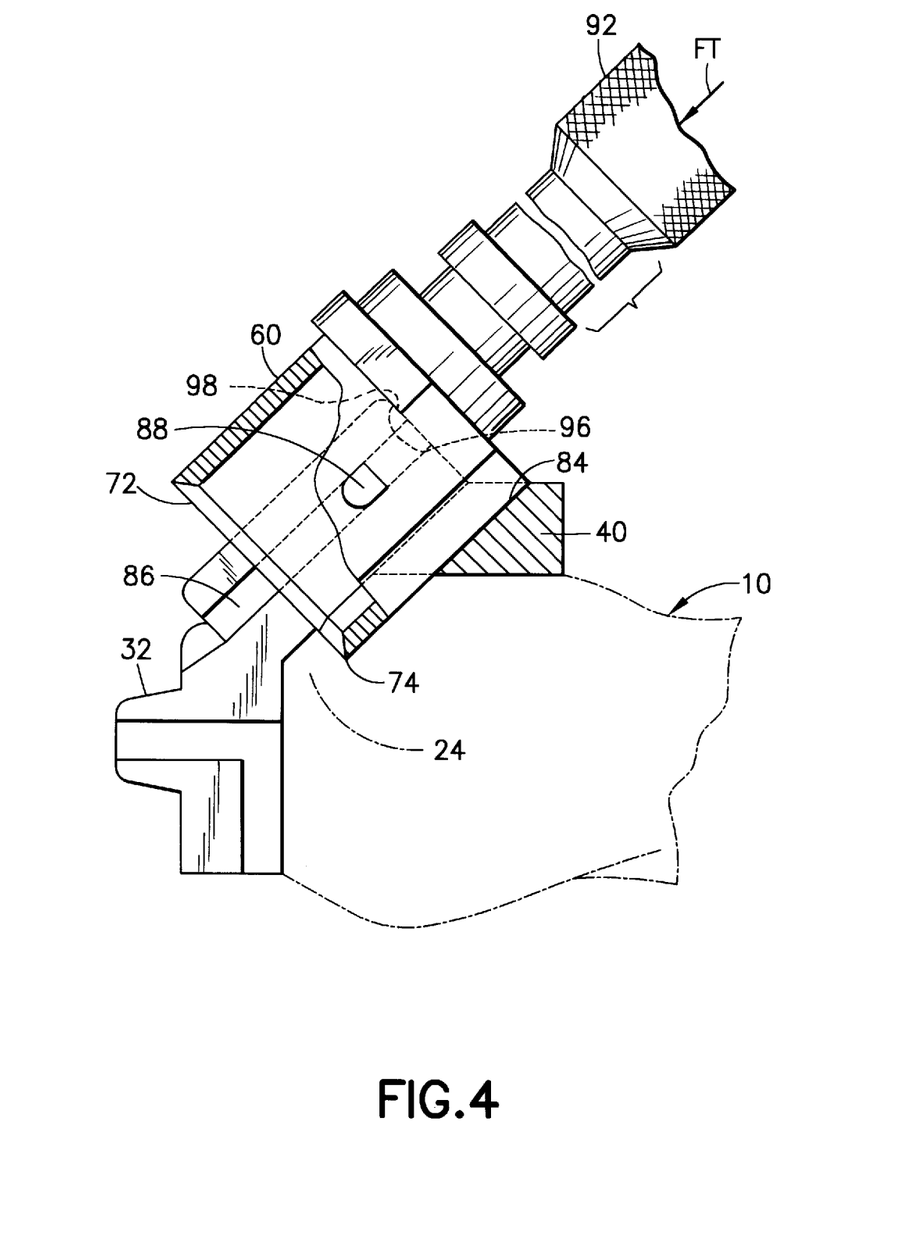
FIG. 4 is a cross-sectional view similar to FIG. 3, showing the component parts in another position.

Upon securing the cutting guide 32 to the distal femur 10, as illustrated in FIG. 2, the cutting punch 60 is inserted into the first channel 80, with the splines 88 engaging the complementary grooves 86, the curved face 64 of the cutting punch 60 confronting the complementary curved bottom 84 of the channel 80, and the cutting edge 70 leading the way through the entrance 82, as seen in FIG. 3, all as facilitated by the attached handle 92. A cutting force FT is applied to the handle 92, and the cutting punch 60 is moved forward to advance the cutting punch 60 along the transverse direction of the channel 80, in a generally distal direction, to the fully advanced position illustrated in FIG. 4, to remove natural bone from the intercondylar area 24 and establish the desired patella recess. The combination of the straight cutting portions 72 and the curved cutting portion 74 of the cutting edge 70, together with the described orientation of the cutting punch 60, assures the establishment of an appropriate patella recess with ease and accuracy. Once the movement of the cutting punch 60 along the first channel 80 in the forward direction completes the patella recess, stop means in the form of a stop shoulder 96 on the cutting punch 60 and a complementary shoulder 98 on the cutting guide 32 are engaged to preclude further advancement of the cutting punch 60 in the cutting guide 32, thereby attaining accuracy with ease and safety. The cutting punch 60 then is retracted from the first channel 80 to be removed from the cutting guide 32.

Figure 5:
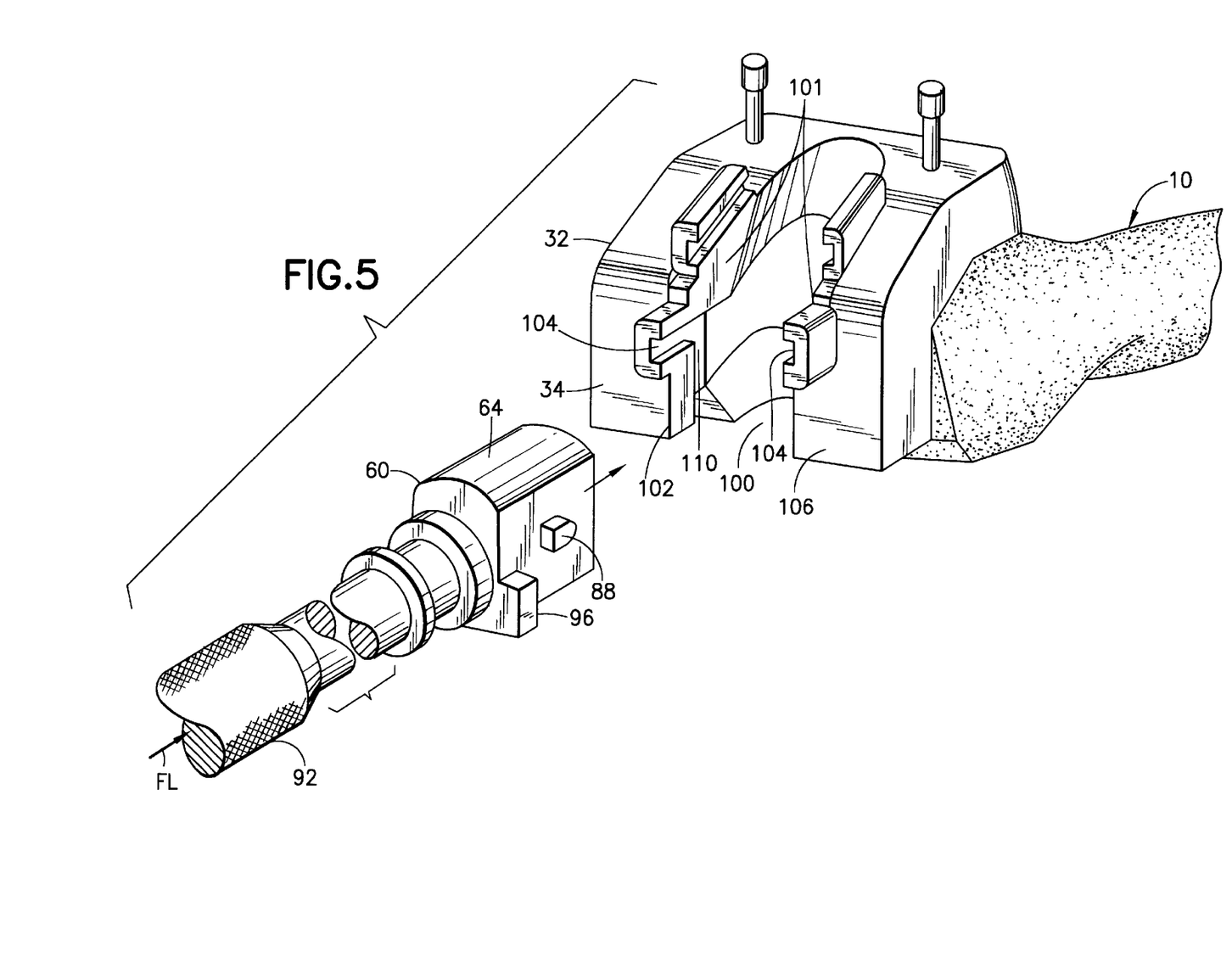
FIG. 5 is a perspective view similar to FIG. 2, showing the component parts in another position.
Figure 6:
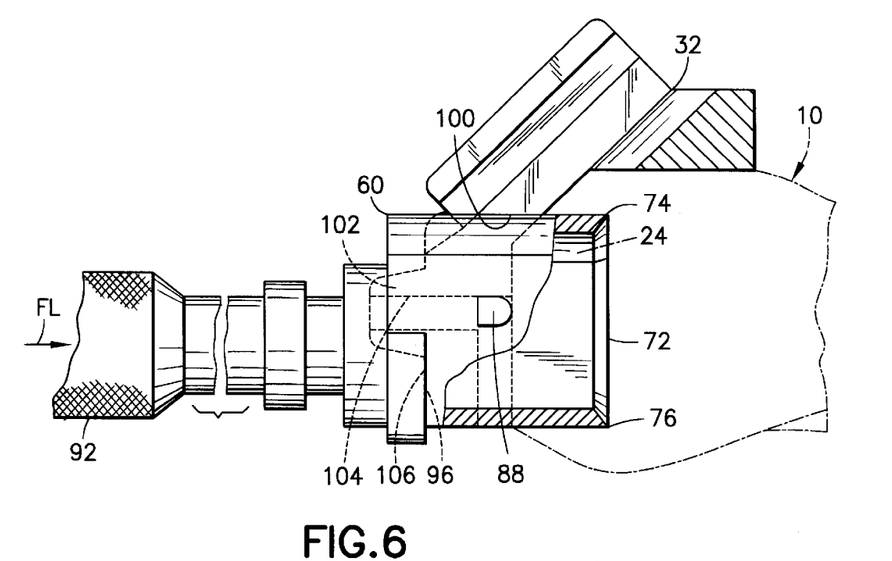
FIG. 6 is a cross-sectional view similar to FIG. 4, showing the component parts in still another position.

Turning now to FIG. 5, cutting guide 32 includes a second channel 100 extending in a longitudinal direction through the first portion 34 of the cutting guide 32, the second channel 100 having a width between opposite laterally spaced apart side walls 101, the width of second channel 100 being generally complementary to the width W of the cutting punch 60, an entrance 102 and a second guideway in the form of second grooves 104 extending longitudinally along the second channel 100 and being complementary to the splines 88 of the cutting punch 60. Upon removal of the cutting punch 60 from the first channel 80, as described above, the cutting punch 60 is inserted into the second channel 100, with the curved face 64 facing upwardly, in the anterior direction, as illustrated in FIG. 5, the splines 88 are engaged in the second grooves 104, and a cutting force FL is applied to the handle 92 of the cutting punch 60 so that the cutting punch 60 is advanced longitudinally, in a generally proximal direction, as seen in FIG. 6, to remove natural bone from the intercondylar area 24 and complete the desired femoral notch. Upon full advancement of the cutting punch 60 within the second channel 100, the stop shoulder 96 on the cutting punch 60 abuts a complementary stop surface 106 on the cutting guide 32 to preclude further advancement of the cutting punch 60 and thereby assure accuracy, with ease and safety, in completing the femoral notch. Again, the combination of the straight cutting portions 72 and 76, and the curved cutting portion 74 of the cutting edge 70, together with the described orientation of the cutting punch 60, assures the establishment of an appropriate femoral notch.

Figure 7:
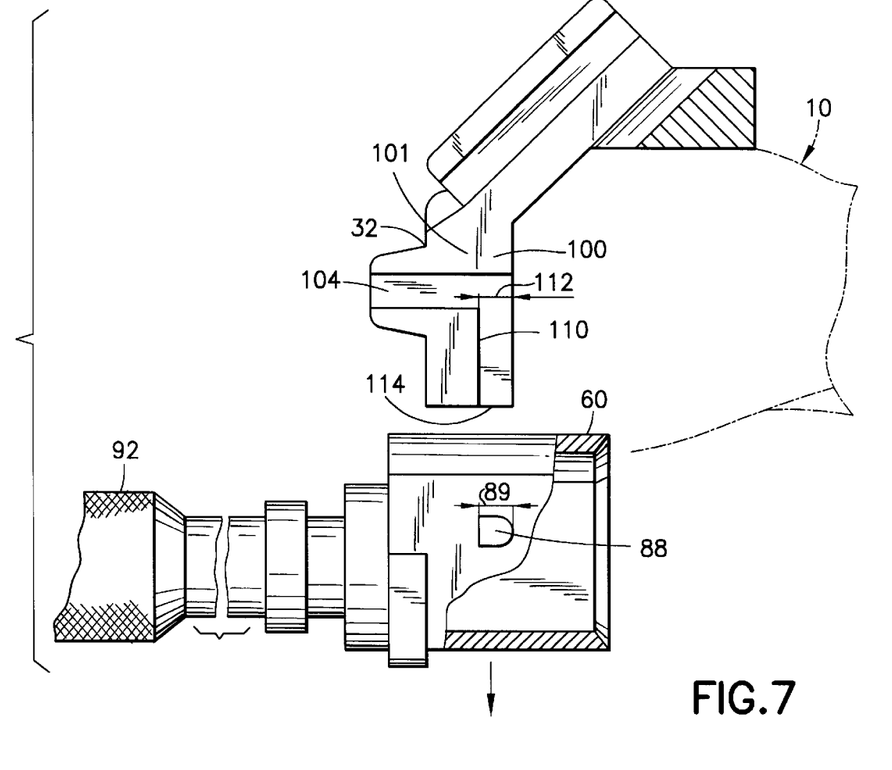
FIG. 7 is a cross-sectional view similar to FIG. 6, showing the component parts in yet another position.

Turning now to FIG. 7, upon full advancement of the cutting punch 60 and completion of the femoral notch, as described in connection with FIGS. 5 and 6, the cutting punch 60 is removed from the second channel 100 by movement in a transverse direction downwardly, in the posterior direction. To this end, the second channel 100 includes a third guideway in the form of third grooves 110 extending transverse to the second grooves 104, the third grooves 110 having a width 112 and intersecting the second grooves 104 such that the splines 88 on the cutting punch 60 are registered with the third grooves 110 and are transferred from the second grooves 104 into the third grooves 110 by movement of the cutting punch 60 transversely downwardly, in the posterior direction, subsequent to full advancement of the cutting punch 60 and completion of the femoral notch. The downward movement of the cutting punch 60, as illustrated in FIG. 7, facilitates the removal of the cutting punch 60 from the cutting guide 32, and enables simplified removal of the natural bone cut from the intercondylar area 24 by the cutting punch 60 during advancement of the cutting punch 60 within the second channel 100, as described above. In the illustrated preferred embodiment, the third guideway is generally perpendicular to the second guideway, with third grooves 110 extending essentially normal to second grooves 104, downwardly, in the posterior direction, and the width 112 of the third grooves 110 is complementary to the length 89 of the splines 88 so that the cutting punch 60, upon being fully advanced along the second grooves 104, merely is moved transverse to the longitudinal direction of the second grooves 104, out of the second grooves 104 and into the third grooves 110, to traverse the third grooves 110 and exit the third grooves 110 at an egress 114 remote from the second grooves 104, thereby disengaging the cutting punch 60 from the cutting guide 32. Any remaining intercondylar bone then may be removed readily with a rongeur, if necessary.

The use of a cutting punch to remove natural bone from the intercondylar area 24 of the distal femur 10 enhances the accuracy with which the femoral notch is formed, as well as enabling such accuracy to be attained in less time. The ability to insert the cutting punch 60 into the cutting guide 32 along first channel 80 to establish the patella recess, and then along the second channel 100 to complete the femoral notch, while the cutting guide 32 remains secured in place on the distal femur 10, further increases accuracy and reduces the time necessary for the completion of the femoral notch, thereby facilitating the preparation of the distal femur 10 for the reception of a posteriorly stabilized femoral component.

It will be seen that the present invention attains the several objects and advantages summarized above, namely: Effects the removal of intercondylar bone with greater ease and increased accuracy for facilitating preparation of the femoral notch; enables the creation of a complete femoral notch, including an appropriate patella recess, more quickly, to the benefit of both the surgeon and the recipient of the prosthetic knee implant; provides an instrument system and method having less complexity for increased ease of use; simplifies the procedure for preparing a distal femur for the reception of a posteriorly stabilized femoral component; enables accuracy in the removal of only that amount of natural bone necessary for proper accommodation of the femoral component, thereby minimizing trauma to the bone while maximizing performance of the femoral component; assures proper fitting of the femoral component for exemplary performance over a long service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An instrument system for preparation of a longitudinally extending distal femur for the implant of a posteriorly stabilized femoral component of a knee prosthesis, the preparation including removal of natural bone in the intercondylar area of the distal femur to prepare a femoral notch, including a patella recess, subsequent to the execution of distal, anterior and chamfer cuts establishing a prepared distal femur having distal, anterior and chamfer surfaces, the instrument system comprising:

a femoral notch cutting guide for placement over the distal, anterior and chamfer surfaces of the prepared distal femur, the femoral notch cutting guide having a first portion including a first surface for overlying the distal surfaces, a second portion including a second surface for overlying the anterior surfaces and a third portion including a third surface for overlying the chamfer surfaces, the femoral notch cutting guide including a first guideway extending along the femoral notch cutting guide in a direction transverse to the longitudinal extent of the distal femur, and a second guideway extending along the femoral notch cutting guide in a generally longitudinal direction; and a femoral notch cutting punch having a length extending between opposite ends, a cutting edge at one of the opposite ends, and coupling means at the other of the opposite ends, the femoral notch cutting punch including follower means extending along the length of the femoral notch cutting punch, the follower means being complementary to each of the first and second guideways such that upon engagement of the follower means with the first guideway and the application of a cutting force at the coupling means the femoral notch cutting punch is advanced transversely, in a generally distal direction, to remove natural bone and establish the patella recess, and upon engagement of the follower means with the second guideway and the application of a further cutting force at the coupling means, the femoral notch cutting punch is advanced longitudinally, in a generally proximal direction, to remove natural bone to complete the femoral notch.

2. The invention of claim 1 wherein the femoral notch cutting guide further includes a third guideway transverse to the second guideway and intersecting the second guideway such that subsequent to advancement of the femoral notch cutting punch within the second guideway to complete the femoral notch, the femoral notch cutting punch is moved transverse to the second guideway, out of the second guideway and into the third guideway for removal of the femoral notch cutting punch from the femoral notch cutting guide.

3. The invention of claim 1 wherein the first guideway extends along the third portion of the femoral notch cutting guide, between the first portion and the second portion.

4. The invention of claim 3 wherein the second guideway extends through the second portion of the femoral notch cutting guide.

5. The invention of claim 4 wherein the femoral notch cutting guide includes a third guideway transverse to the second guideway and intersecting the second guideway such that subsequent to advancement of the femoral notch cutting punch within the second guideway to complete the femoral notch, the femoral notch cutting punch is moved transverse to the second guideway, out of the second guideway and into the third guideway for removal of the femoral notch cutting punch from the femoral notch cutting guide.

6. The invention of claim 5 wherein the third guideway is essentially perpendicular to the second guideway and extends downwardly, in a posterior direction, the third guideway including an egress remote from the second guideway, through which egress the follower means is passed to remove the femoral notch cutting punch from the femoral notch cutting guide.

7. The invention of claim 1 further including stop means on the femoral notch cutting guide and on the femoral notch cutting punch, the stop means including a stop for precluding advancement of the femoral notch cutting punch beyond a predetermined fully advanced position along the first guideway.

8. The invention of claim 7 wherein the stop means includes a further stop for precluding advancement of the femoral notch cutting punch beyond a further predetermined fully advanced position along the second guideway.

9. The invention of claim 8 wherein the stop means include a stop shoulder on the femoral notch cutting punch.

10. The invention of claim 1 wherein:
the femoral notch cutting punch has opposite sides spaced apart laterally to establish a predetermined width;
the first guideway includes a first channel extending along the femoral notch cutting guide, the first channel having opposite side walls spaced apart laterally complementary to the predetermined width of the femoral notch cutting punch to receive the femoral notch cutting punch in sliding engagement, and a groove in each side wall, the grooves extending in the direction of the first guideway; and
the follower means includes a spline along each of the opposite sides of the femoral notch cutting punch, the splines being complementary to the respective grooves in each side wall of the channel for guiding the femoral notch cutting punch in the transverse, generally distal direction in response to the application of the cutting force.

11. The invention of claim 10 wherein the second guideway includes a second channel extending along the femoral notch cutting guide, the second channel having opposite side walls spaced apart laterally complementary to the predetermined width of the femoral notch cutting punch to receive the femoral notch cutting punch in sliding engagement, and a further groove in each side wall of the second channel, the further grooves extending in the direction of the second guideway;
the splines being complementary to the respective further grooves in each side wall of the second channel for guiding the femoral notch cutting punch in the generally longitudinal direction in response to the application of the further cutting force.

12. The invention of claim 11 including stop means on the femoral notch cutting guide and on the femoral notch cutting punch, the stop means including a stop for precluding advancement of the femoral notch cutting punch beyond a predetermined fully advanced position along the first guideway.

13. The invention of claim 12 wherein the stop means includes a further stop for precluding advancement of the femoral notch cutting punch beyond a further predetermined fully advanced position along the second guideway.

14. The invention of claim 13 wherein the splines have a predetermined length along the femoral notch cutting punch, and the femoral notch cutting guide includes a third guideway transverse to the second guideway and intersecting the second guideway such that subsequent to advancement of the femoral notch cutting punch within the second guideway to complete the femoral notch, the femoral notch cutting punch is moved transverse to the second guideway, out of the second guideway and into the third guideway for removal of the femoral notch cutting punch from the femoral notch cutting guide, the third guideway including still further grooves extending in the direction of the third guideway, the still further grooves having a width complementary to the predetermined length of the splines so as to permit movement of the splines through the further grooves in a direction transverse to the length of the splines.

15. The invention of claim 1 wherein the cutting edge of the femoral notch cutting punch includes essentially parallel opposite generally straight cutting portions, a further generally straight cutting portion extending between the opposite generally straight cutting portions, and a curved cutting portion extending between the opposite generally straight cutting portions, opposite the further generally straight cutting portion.

16. An instrument system for preparation of a longitudinally extending natural bone for the implant of a component of a prosthesis at a site on the natural bone, the preparation including removal of natural bone to prepare a notch in the natural bone subsequent to the execution of cuts establishing at least a longitudinally extending surface and a laterally extending surface at the site on the natural bone, the instrument system comprising:
a notch cutting guide for placement over the longitudinally extending surface and the laterally extending surface at the site, the notch cutting guide having surfaces for overlying the longitudinally extending surface and the laterally extending surface at the site on the natural bone, the notch cutting guide including a first guideway extending along the notch cutting guide in a direction transverse to the longitudinal extent of the natural bone, and a second guideway extending along the notch cutting guide in a generally longitudinal direction; and
a notch cutting punch having a length extending between opposite ends, a cutting edge at one of the opposite ends, and coupling means at the other of the opposite ends, the notch cutting punch including follower means extending along the length of the notch cutting punch, the follower means being complementary to each of the first and second guideways such that upon engagement of the follower means with the first guideway and the application of a cutting force at the coupling means the notch cutting punch is advanced transversely, to remove natural bone and establish a portion of the notch, and upon engagement of the follower means with the second guideway and the application of a further cutting force at the coupling means, the notch cutting punch is advanced longitudinally, to remove natural bone to complete the notch.

17. The invention of claim 16 wherein the notch cutting guide further includes a third guideway transverse to the second guideway and intersecting the second guideway such that subsequent to advancement of the notch cutting punch within the second guideway to complete the notch, the notch cutting punch is moved transverse to the second guideway, out of the second guideway and into the third guideway for removal of the notch cutting punch from the notch cutting guide.

* * * * *